(12) United States Patent
Boliek et al.

(10) Patent No.: US 12,112,124 B1
(45) Date of Patent: Oct. 8, 2024

(54) COMPUTING SYSTEM FOR GENERATING CUSTOMIZED HEALTH FORM BASED ON CLINICAL DATA

(71) Applicant: Allscripts Software, LLC, Raleigh, NC (US)

(72) Inventors: Caroline Boliek, Raleigh, NC (US); Ross C. Teague, Cary, NC (US); Andrew Burka, Raleigh, NC (US); David Windell, Raleigh, NC (US)

(73) Assignee: ALTERA DIGITAL HEALTH INC., Niagara Falls, NY (US)

( * ) Notice: Subject to any disclaimer, the term of this patent is extended or adjusted under 35 U.S.C. 154(b) by 105 days.

(21) Appl. No.: 16/230,241

(22) Filed: Dec. 21, 2018

(51) Int. Cl.
| | |
|---|---|
| *G06F 40/186* | (2020.01) |
| *G06F 40/109* | (2020.01) |
| *G16H 10/60* | (2018.01) |
| *G16H 15/00* | (2018.01) |

(52) U.S. Cl.
CPC .......... *G06F 40/186* (2020.01); *G06F 40/109* (2020.01); *G16H 10/60* (2018.01); *G16H 15/00* (2018.01)

(58) Field of Classification Search
CPC ...... G06F 40/186; G16H 10/60; G16H 15/00; G04F 40/109
USPC ........................................................ 715/223
See application file for complete search history.

(56) References Cited

U.S. PATENT DOCUMENTS

| | | | |
|---|---|---|---|
| 5,572,421 A | 11/1996 | Altman et al. | |
| 6,607,482 B1 | 8/2003 | Teitelbaum | |
| 2002/0022975 A1* | 2/2002 | Blasingame | G16H 40/67 |
| | | | 705/3 |
| 2002/0035486 A1 | 3/2002 | Huyn et al. | |
| 2002/0138462 A1* | 9/2002 | Ricketts | G06F 40/174 |
| 2003/0004788 A1 | 1/2003 | Edmundson et al. | |
| 2003/0171660 A1 | 9/2003 | Foster, Jr. | |
| 2004/0243586 A1* | 12/2004 | Byers | G16H 10/60 |
| 2009/0138284 A1* | 5/2009 | Guadagna | G06Q 10/10 |
| | | | 705/3 |
| 2013/0235073 A1* | 9/2013 | Jaramillo | G09G 5/00 |
| | | | 345/619 |
| 2015/0213414 A1* | 7/2015 | Zuckerman | G06Q 10/1095 |
| | | | 705/7.19 |
| 2015/0321000 A1* | 11/2015 | Rosenbluth | A61N 1/08 |
| | | | 607/48 |
| 2017/0000342 A1* | 1/2017 | Samec | G02B 27/0179 |

* cited by examiner

*Primary Examiner* — Mohammed H Zuberi
*Assistant Examiner* — Tionna M Burke
(74) *Attorney, Agent, or Firm* — CALFEE, HALTER & GRISWOLD LLP

(57) ABSTRACT

A computing system that facilitates generating customized health forms for a patient is disclosed herein. Subsequent to receiving a patient identifier from a client computing device, a server electronic health records application (EHR) transmits clinical data assigned to the patient identifier to a server health form application. Based on the clinical data assigned to the patient, the server health form application generates a customized health form for the patient using form data. The server health form application then transmits the customized health form to a client health form application for presentment on a display of the client computing device. The server health form application updates the customized health form for the patient as the patient responds to questions and as the server health form application receives sensor data from the client computing device.

17 Claims, 6 Drawing Sheets

COMPUTING SYSTEM FOR GENERATING CUSTOMIZED HEALTH FORM BASED ON CLINICAL DATA

BACKGROUND

Electronic health record applications (EHRs) are computer-executable applications utilized in healthcare environments. EHRs are generally configured to perform various tasks related to healthcare including patient intake tasks, scheduling tasks, insurance processing tasks, billing tasks, health record maintenance tasks, and so forth. EHRs are often used by healthcare workers at the point of care (i.e., at a time when the healthcare worker is providing care to a patient). For example, a healthcare worker (e.g., a physician) may retrieve clinical data from a patient record maintained by an EHR to relatively quickly ascertain problems being experienced by the patient, medications currently taken by the patient, and so forth.

It is understood that to generate a complete patient record, clinical data must be collected from the patient directly. As such, a variety of health forms have been developed over time, some electronic and some paper based. Broadly speaking, a health form targets specific clinical information about the patient (e.g., patient demographics, heart health, reproductive health, etc.) that is important to give a healthcare worker an accurate understanding of the patient's overall health.

There are various deficiencies associated with conventional electronic health forms. First, conventional electronic health forms are typically not configured to exchange data (e.g., clinical data) with an EHR. Additionally, even when conventional electronic health forms can exchange data with the EHR, the electronic health form does not alter the health forms being generated based on the shared clinical data. Rather, the same health form is presented to a patient regardless of eyesight ability, native language, or known health information.

SUMMARY

The following is a brief summary of subject matter that is described in greater detail herein. This summary is not intended to be limiting as to the scope of the claims.

Described herein are various technologies pertaining to a computing system for patient record maintenance. More specifically, an electronic health records application (EHR) is described herein, wherein the EHR includes server-side functionality (server EHR). A health form application is also described herein, wherein the health form application is a distributed application that includes server-side functionality (server health form application) and client-side functionality (client health form application). The EHR and the health form application can work in conjunction with one another to facilitate generating a customized health survey for a patient to mine clinical data pertaining to the patient. The EHR can also provide clinical decision support for the patient based on the clinical data collected by the health form application.

In operation, the client health form application executes on a client computing device operated by the patient. The server health form application executes on a server computing device. The client health form application is in network communication with the server health form application. The client health form application receives input from a healthcare worker indicative of an identifier for the patient. The client health form application may then transmit the identifier for the patient and an indication that a customized health form is required to the server EHR.

The server EHR causes clinical data assigned to the patient identifier to be transmitted to the server health form application, which generates a customized health form for the patient based upon the clinical data. More specifically, the server EHR receives the identifier for the patient. The server EHR may then execute a search over clinical data retained in a data store accessible by the server EHR for clinical data assigned to the patient identifier. The clinical data comprises demographic information, medication history, medical procedure history, etc. The clinical data assigned to the patient is then transmitted to the server health form application. Based on the clinical data, the health form application generates a list of recommended health questions from form data stored in a database accessible to the server health form application, which comprises health questions designed to collect specific clinical data regarding a patient. The server health form application then transmits a list of recommended health questions to the client health form application, wherein the healthcare worker selects which health questions the patient should complete. Subsequent to receiving the selection of health questions the healthcare worker requires the patient fill out, the server health form application generates a customized health form specifically designed for that patient comprising the selected health questions, which it transmits to the client health form application for presentment on a display of the client computing device for the patient to complete.

The client health form application receives input from the patient comprising responses to the customized health form. The client health form application then transmits the responses to the server health form application. As the server health form application receives the responses, it can identify additional questions to gather additional data and transmit them to the client health form application to generate an updated customized health form based on the responses received. Additionally, as the patient completes the customized health form, sensors housed in the client computing device generate sensor data including sensor data collected from microphones, cameras, gyroscopic sensors, heat sensors, etc. The sensors transmit the sensor data to the client health form application, which then transmits the sensor data to the server health form application. The sensor data can be used by the server health form application to generate additional questions to provide to the client health form application for the patient to answer.

After the server health form application receives responses to the customized health form and updates customized health form and the responses have been reviewed by a healthcare worker to ensure completion, the server health form application transmits the responses to the server EHR to be stored in the database maintained by the server EHR as clinical data indexed to the patient identifier.

The above-described technologies present various advantages over conventional health form applications. First, unlike conventional health form applications, the above-described system is configured to generate customized health forms targeted to avoid redundant questioning and collect new clinical data through the use of existing clinical data stored in a database and sensor data received from a client computing device. Second, the above-described technologies enable clinical data for the patient collected via the health form application to be integrated directly into a patient record for the patient without having to be imported, which is advantageous from a data processing perspective.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
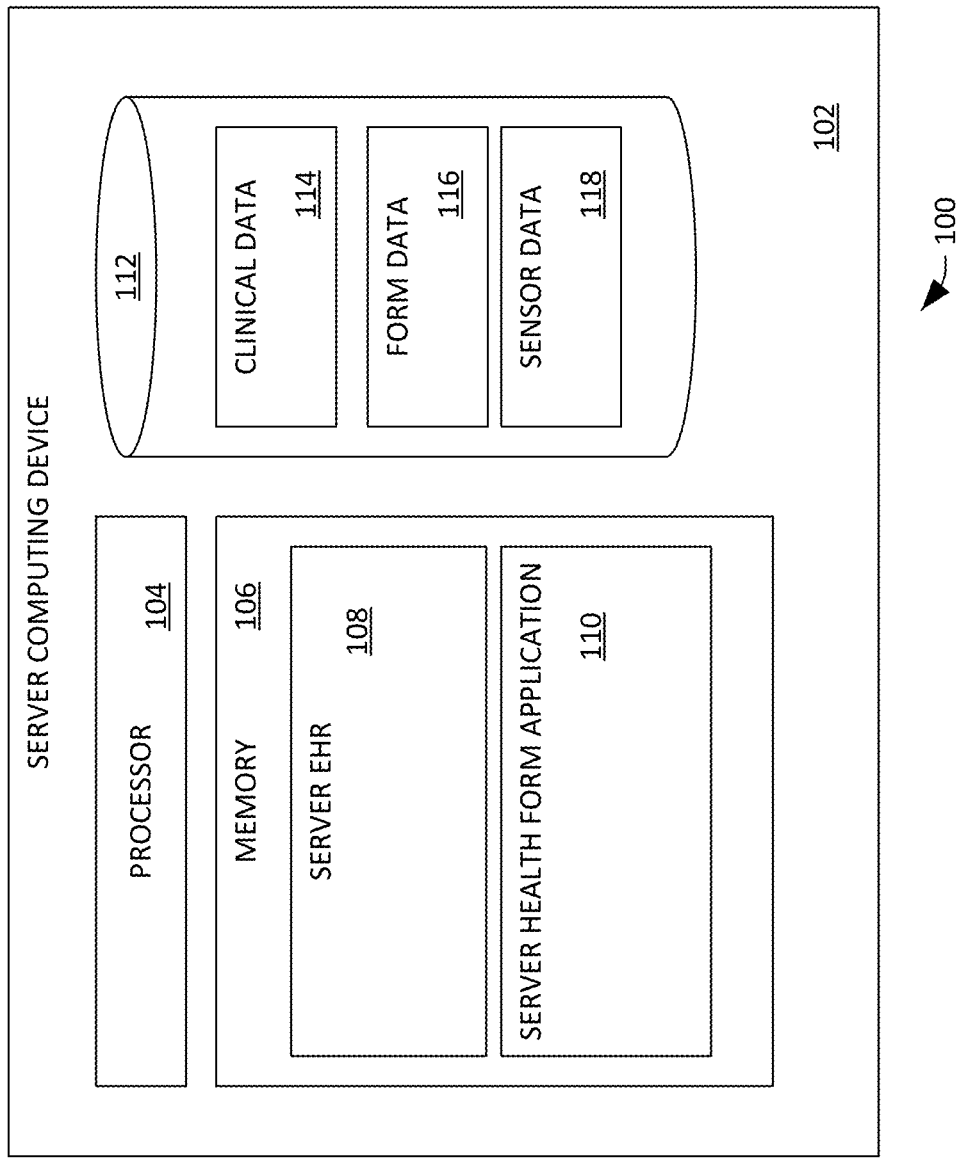
FIG. 1 is a functional block diagram of an exemplary computing system that facilitates generating a customized health form for a patient and integrating the resulting data into a patient record.

Various technologies pertaining to generating a customized health form based on clinical data from a patient record for a patient is now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A: X employs B: or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

With reference to FIG. 1, an exemplary computing system 100 that facilitates generating a customizable health form designed to collect patient health data and integrating the patient health data into a patient record is illustrated. The computing system 100 includes a server computing device 102. The server computing device 102 comprises a processor 104 and memory 106, wherein the memory 106 has a server electronic health records application (server EHR) 108 and server health form application 110 loaded therein. In general, the server EHR 108 is configured to perform a variety of tasks related to patient healthcare (e.g., patient intake, prescription generation, patient record creation and maintenance, etc.). The server health form application 110 is generally configured to generate customized health forms for a patient based on clinical data received from the server EHR 108. The server health form application 110 is additionally configured to update the customized health form based on sensor data received from a client computing device operated by a patient.

The server computing device 102 additionally includes a data store 112. The data store 112 comprises clinical data 114, form data 116, and sensor data 118. The clinical data 114 for patients may include demographic information, diagnosis data, treatment data, identities of medications taken by patients, identities of allergies, family medical history information, identities of laboratory tests, and/or notes with respect to patient encounters.

The form data 116 comprises rules that, when provided with the clinical data 114 of a specific patient, dictates content of an electronic form, such that the electronic form is customized for the patient. In a non-limiting example, the form data includes a rule indicating that if the family medical history in the clinical data of the patient indicates a history of glaucoma, the server health form application 110 will include a question in an electronic form about eyesight of the patient. In another example, a rule indicates that if the clinical data of the patient indicates that the patient was previously prescribed a particular medication, questions regarding symptoms the medication should be correcting will be included in the customized health form. Health information forms are standard health forms targeted to acquire health information about a patient. For example, conventionally, when a patient enters a medical office, an in-take specialist gives the patient a stack of paperwork to fill out. The form data 116 comprises digital versions of those forms, as well as additional questions curated by an office, hospital, healthcare worker, or the like. In a non-limiting example, the form data 116 may include questions targeted toward collecting demographic data, mental wellness data, colon health data, stomach health data, skin health data, eye health data, etc. The form data 116 can be combined in any sequence to create a customized health form for a patient to complete.

The sensor data 118 comprises data received from sensors on a client computing device in network communication with the server computing device 102. More specifically, the sensor data 118 can include gyroscope sensor data monitoring the client computing device's position in space, camera data, microphone data, temperature data, etc. The sensor data 118 is processed by the server health form application 110 as the sensor data 118 is received from the sensors to identify the potential cause of sensor data 118 received from the client computing device (e.g., if the sensor data comprises a signal from the gyroscope corresponding to rapid, small movement, the server health form application 110 can flag potential tremors).

Figure 2:
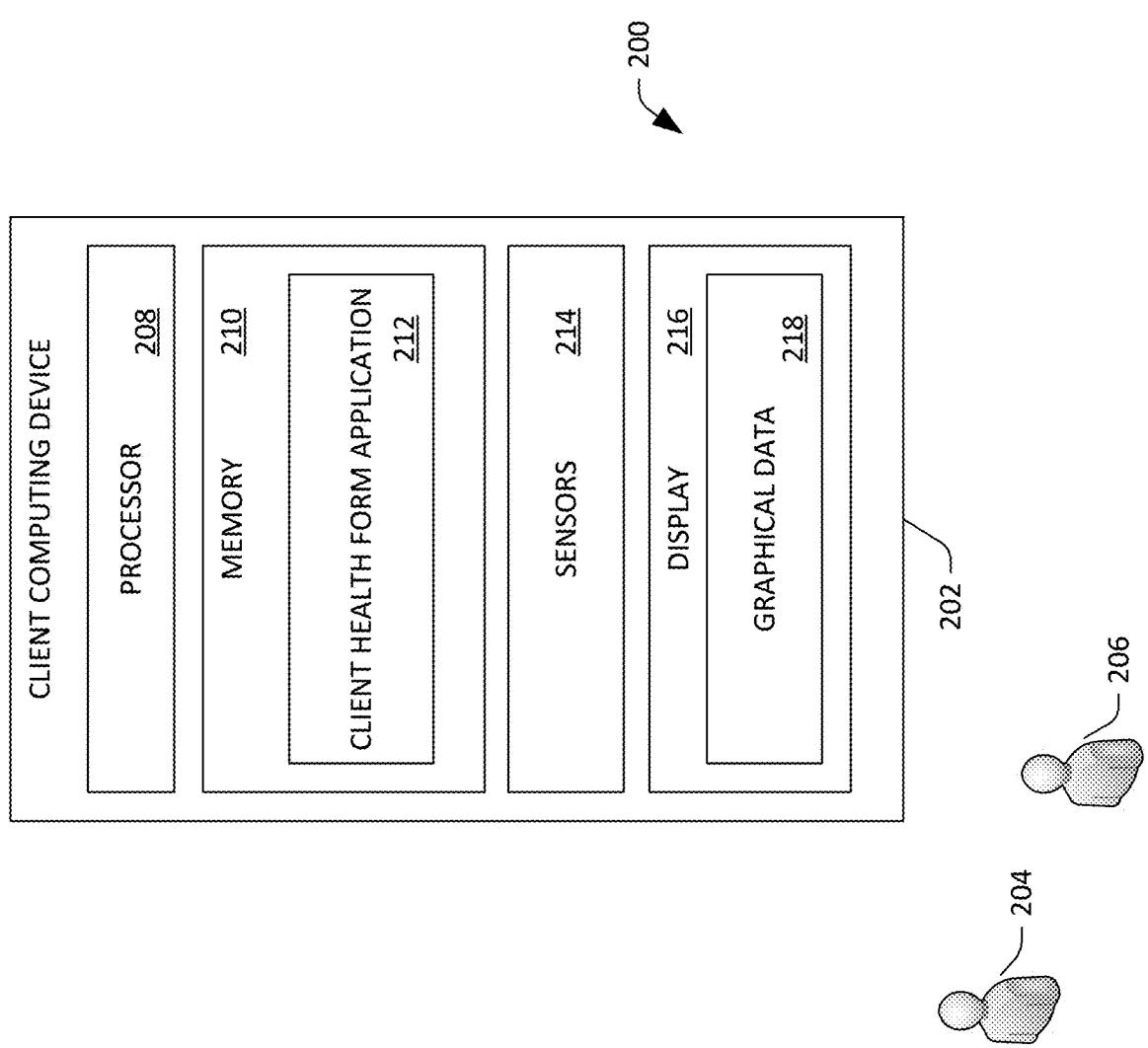
FIG. 2 is a functional block diagram of an exemplary client computing device.

Referring briefly now to FIG. 2, the computing system 100 additionally includes a client computing device 202 operated first by a healthcare worker 204 (e.g., clinician, nurse, patient in-take specialist, etc.) and second by a patient 206. The client computing device 202 is in communication with the server computing device 102 by way of a network (e.g., the Internet, intranet, etc.). In an example, the client computing device 202 may be a desktop computing device, a laptop computing device, or a mobile computing device such as a tablet computing device or smartphone.

The client computing device 202 comprises a processor 208 and memory 210, wherein the memory 210 has a client health form application 212 loaded therein. In general, the client health form application 212 is configured to interface with the server health form application 110, which in turn is configured to interface with the server EHR 108, thereby providing the user with access to the functionality of the server health form application 110, which can receive clinical data from the server EHR 108.

The client computing device 202 also includes sensors 214, which comprise a plurality of sensors, including, but not limited to, a sensor suitable for detecting touch input on a display (such as a capacitive sensor), a sensor suitable for detecting key-presses, a gyroscope, an RGB camera, a microphone, a GPS sensor, an IR camera, a depth sensor, and so forth. Additionally, the client computing device 202 includes a display 216, whereupon graphical data 218 (e.g., a graphical user interface (GUI) of the client health form application 212) may be presented thereon.

Referring generally now to FIGS. 1-2, exemplary operation of the computing system comprising the server computing device 102 and the client computing device 202 is now set forth. It is contemplated that the patient 206 needs to fill out a variety of health forms provided by a health organization that maintains the EHR and the health form application. As such, the healthcare worker 204 configures the client computing device 202 to display the appropriate health forms to the patient 206 via the client health form application 212. The client health form application 212 executing on the client computing device 202 receives user credentials (e.g., username and password) from the healthcare worker 204, and the client health form application 212 causes the client computing device 202 to transfer the user credentials to the server computing device 102. The server health form application 110 receives the user credentials and the server health form application 110 authenticates the healthcare worker 204. Responsive to the server health form application 110 authenticating the user credentials of the healthcare worker 204, the client computing device 202 receives, from the healthcare worker 204, an identifier for a patient 206 and an indication that a customized health form is to be generated for the patient 206. The identifier for the patient 206 and the indication that a customized health form is to be generated for the patient 206 can be received based upon one user interaction with the client health form application 212 or multiple user interactions with the client health form application 212. Responsive to receipt of the identifier for the patient 206 and the indication, the client health form application 212 transmits the identifier for the patient to the server health form application 110 as well as the indication that the customized health form is to be generated for the patient 206.

The server health form application 110, responsive to receiving the indication that the customized health form is to be generated for the patient 206, transmits the patient identifier to the server EHR 108. The server EHR 108 searches the clinical data 114 for clinical data that is assigned to the identifier for the patient 206. For instance, the server EHR 108 can retrieve an electronic health record for the patient 206 from the clinical data 114 based upon the identifier for the patient 206. The clinical data includes demographic data, medication history, medical diagnoses, etc. for the patient. Once the server EHR 108 has located clinical data assigned to the patient identifier, the server EHR 108 transmits the clinical data assigned to the patient identifier to the server health form application 110, which then generates a customized health form for the patient 206 based upon the clinical data assigned to the patient 206. The server health form application 110 then transmits the customized health form to the client computing device 202, where it is received by the client health form application 212 and displayed on the display 216.

Upon receipt of the clinical data assigned to the patient, the server health form application 110 provides the form data 116 with the clinical data assigned to the patient. The form data 116 comprises rules that, when provided with the clinical data assigned to the specific patient, dictates content of an electronic form, such that the electronic form is customized for the patient. The form data 116 may include questions targeted toward collecting demographic data, mental wellness data, colon health data, stomach health data, skin health data, eye health data, etc. In a non-limiting example, the clinical data assigned to the patient may indicate the patient is a 50-year-old male with a family history of colon cancer who hasn't filled out a general health information form in two years. The server health form application 110 uses the form data 116 and the clinical data assigned to the patient to generate a list of health questions recommended that the patient complete, which, in this example, would include demographic data questions, general health questions, and colon health questions. The server health form application 110 also searches over clinical data assigned to the patient stored as clinical data 114 in the database 112 for pertinent display information. For example, the demographic data within the clinical data assigned to the patient may indicate that the patient's primary language is Spanish. In this case, a rule in the form data 116 causes the server health form application 110 to provide the customized health form in Spanish. Similarly, if the patient is elderly, the server health form application 110 generates the customized health form such that they are presented in a higher point font for ease of readability.

The server health form application 110 transmits the list of recommended health questions, which can be a series of related health questions, to the client health form application 212. The client health form application 212 presents the list of recommended health questions on the display 216 of the client computing device 202 as graphical data 218. Responsive to input comprising a selection of health questions from the list of recommended health questions presented on the display 216, the client health form application 212 transmits the identities of the selected health questions to the server health form application 110 executing on the server computing device 102. Responsive to receiving the indication of which health questions are required, the server health form application 110 searches over form data 116 maintained in a database of the server computing device 102 for the identified health questions. The identified health questions are then combined by the server health form application 110 into a single customized health form for the patient, which the server health form application 110 then transmits to the client health form application 212 for presentment on the display 216 of the client computing device 202 as graphical data 218.

Once the customized health form is loaded on the display 216, the patient 206 completes the customized health form by providing responses to each question as prompted. Once the client health form application 212 has received an input that comprises a response to each question of the customized health form, and subsequent to review by the healthcare worker 204, the client health form application 212 transmits the responses to the server health form application 110, which then transmits the responses to the server EHR 108, which in turn stores the responses as clinical data assigned to the patient within the clinical data 114 maintained in the database 112.

As the patient 206 completes the customized health form, the sensors 214 on the client computing device 202 generate sensor data from a variety of sensors within the client computing device 202. The sensors can include camera, microphone, gyroscopes, etc. The client health form application 212 receives the sensor data and subsequently transmits the collected sensor data to the server health form application 110. The server health form application 110 can process the sensor data and identify potential health origins for the sensor data and adjust the customized health form accordingly. For example, if the patient is squinting while completing the customized health form being presented on the display 216, a camera on the client computing device 202 can perceive the squinting. The client health form application 212 can then transmit that information to the server health form application 110, which will provide instructions to the client health form application 212 to increase the font size of the customized health form and also update the customized health form by transmitting additional questions regarding eye health to the client health form application 212. In another example, if the patient 206 presents complaining of chronic pain and is shaking, experiencing cold sweats and exhibiting rapid eye movement, the server health form application 110 will transmit data to the server EHR indicating potential drug seeking behaviors.

Additionally, as the patient 206 completes the customized health form, the client health form application 214 can transmit follow up questions based on the received responses to the customized health form, to create an updated customized health form. For example, if on one response a patient complains of frequent loss of energy during mundane activities and light-headedness, the server health form application can transmit follow up questions relating to heart disease to provide possible clinical decision support to the healthcare worker 204.

The health form application (on the client and server) exhibits various advantages over conventional health form tools. For instance, the server health form application 110 generates the customized health form in a language and format understood by the patient for display on the client computing device without any input from the healthcare worker 204, which reduces the time spent by the patient answering questions and increases accuracy while flagging potential health issues for the healthcare worker 204. Further, the sensor data can be used by a clinical decision support engine, in conjunction with clinical data collected by the health form application, to provide clinical decision support. The clinical decision support can include, but is not limited to, highlighting potential issues for the clinician or causing the health form application to generate more health questions regarding based on responses to previously presented health questions to collect more clinical data. Still further, the customized health form can be updated as the patient is completing it, based on answers received to already completed questions. Finally, the server health form application 110 can link the customized health form to the electronic health record of the patient, which can be readily accessed during future patient encounters for diagnostic reference.

Figure 3:
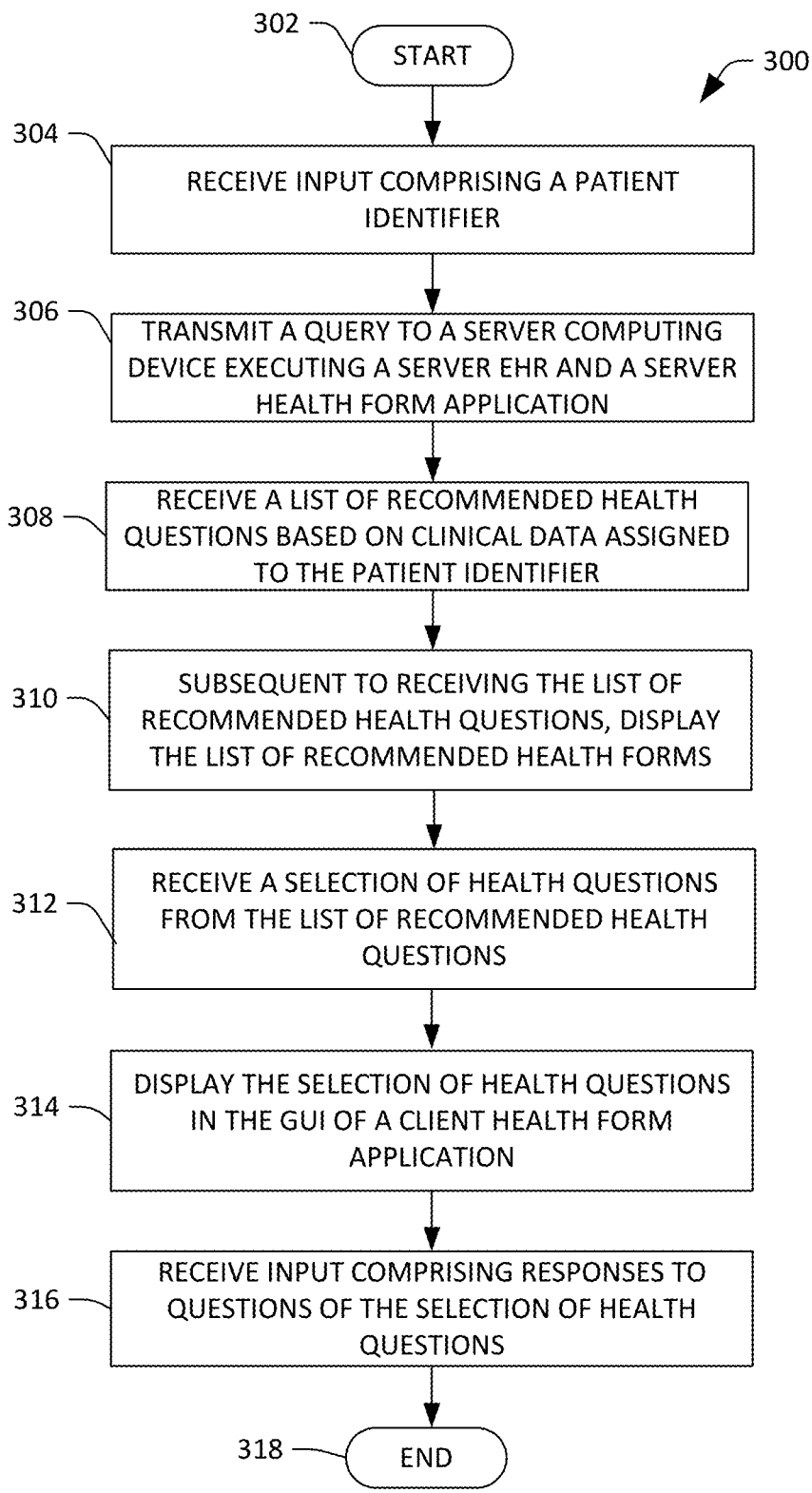
FIG. 3 is a flow diagram that illustrates an exemplary methodology executed by a client electronic health records application for generating a customized health form for a patient.
Figure 4:
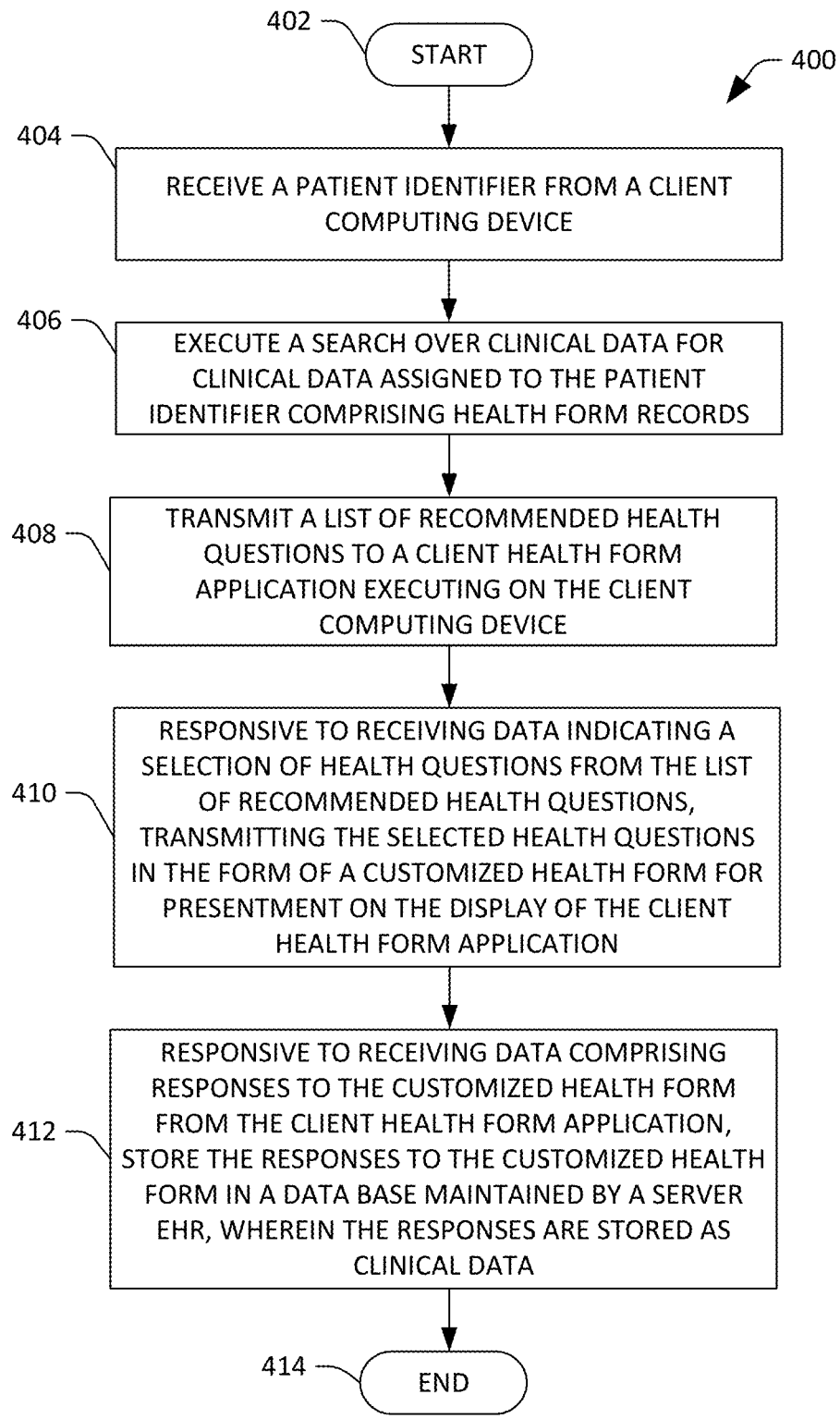
FIG. 4 is a flow diagram that illustrates an exemplary methodology executed by a server health form application for generating a customized health form for a patient.
Figure 5:
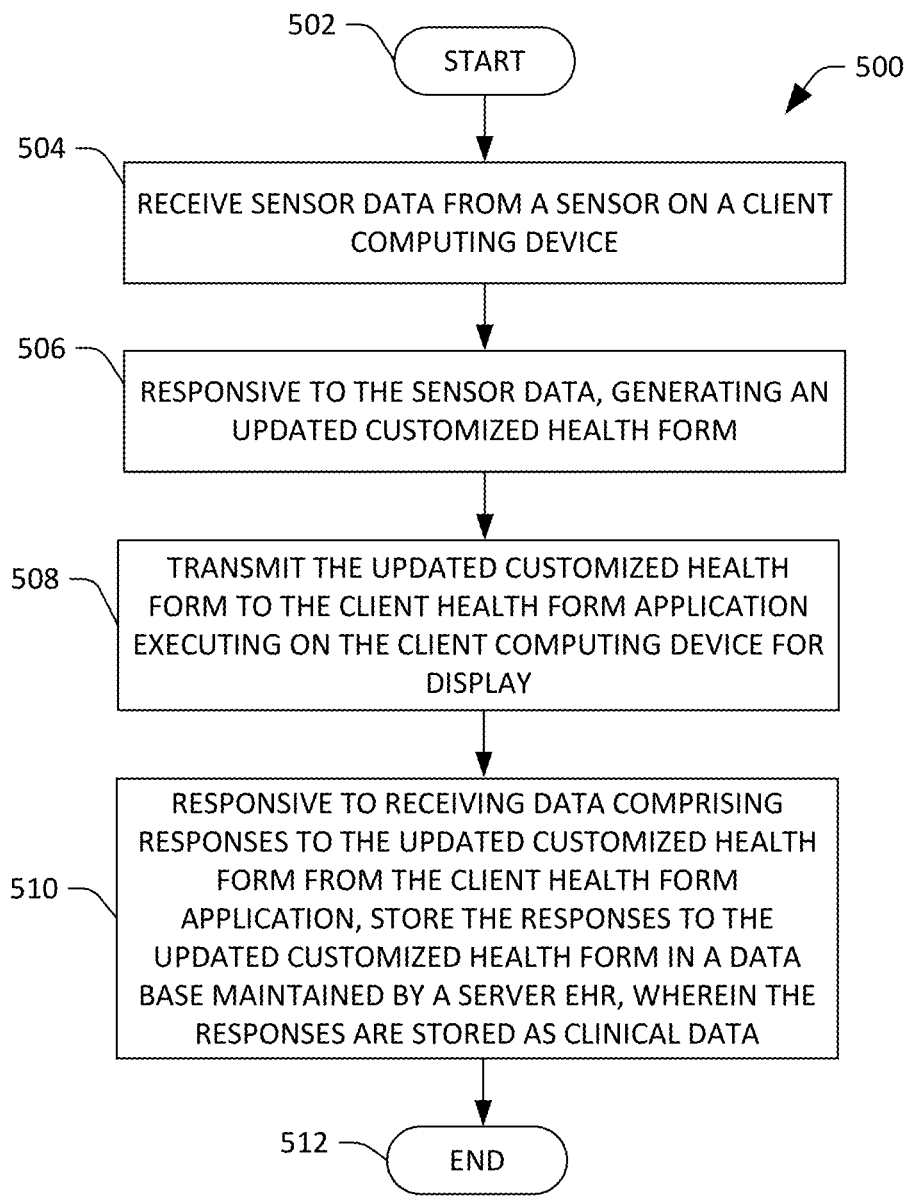
FIG. 5 is a flow diagram that illustrates an exemplary methodology executed by a server health form application for updating a customized health form for a patient based on sensor data received from a client computing device.

FIGS. 3-5 illustrate exemplary methodologies relating to a computing system for generating customized health forms. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

With reference now to FIG. 3, a methodology 300 executed by a client computing device that facilitates generating a customized health form is illustrated. The methodology 300 begins at 302, and at 304, a client health form application receives input comprising a patient identifier and. At 306, responsive to receiving the patient identifier, the client health form application transmits the patient identifier to a server health form application, which then transmits a query to a server EHR for clinical data assigned to the patient identifier. The server EHR maintains a database comprising the clinical data, including clinical data assigned to the patient identifier. The clinical data assigned to the patient identifier provided to the server health form application, which uses a series of rules to identify health questions needed to be filled out by the patient. For example, if the patient is over 50, health questions relating to colon health and colon cancer screenings will be identified. At 308, the client health form application receives the list of recommended health questions identified based on the clinical data assigned to the patient identifier. At 310, the client health form application displays the list of recommended health questions to the user, in this case, a healthcare worker or patient intake professional or the like. At 312, the user selects health questions from the list of recommended health questions that the patient needs to fill out, which is in turn transmitted to the server health form application. At 314, the client health form application displays the selected health questions, which were combined into a customized health form for the patient by the server health form application and transmitted to the client health form application for display on the GUI of the client health form application. At 316, the client health form application receives inputs comprising responses to the questions on the customized health form. The methodology 300 concludes at 318.

Turning now to FIG. 4, a methodology 400 executed by a server computing device that facilitates generating a customized health form for a patient based on clinical data is illustrated. The methodology 400 begins at 402, and at 404, a server health form application executing on a server computing device receives a patient identifier from a client health form application executing on a client computing device to a server EHR. At 406, based on the patient identifier, the server EHR executes a search over clinical data stored in a database maintained by the server EHR for clinical data assigned to the patient identifier. The server EHR transmits the clinical data assigned to the patient identifier to a server health form application, which determines a list of health questions the patient should complete by using a series of rules as applied to the clinical data assigned to the patient identifier. For example, if the patient is over 50, a rule within the server health form application will recommend colon health related forms. At 408, the server health form application transmits the identified recommended health questions for the patient to the client health form application for presentment on a display for the client health form application. Subsequently, at 410, the server health form application, responsive to receiving a selection of health questions from the list of recommended health questions, combines the selected health questions into a customized health form for the patient, which the server health form application transmits to the client health form application for display. At 412, responsive to receiving data comprising responses to the customized health form from the client health form application, the server health form application transmits the responses to the server EHR, wherein the responses are stored as clinical data assigned to the patient identifier. The methodology 400 concludes at 414.

Turning now to FIG. 5, a methodology 500 executed by a server computing device that facilitates generating an updated customized health form for a patient based on sensor data is illustrated. The methodology 500 begins at 502, and at 504, a server health form application executing on a server computing device receives sensor data from a client health form application, which received the sensor data from a sensor on a client computing device. At 506, responsive to the sensor data, the server health form application generates an updated customized health form. For example, if the patient is shaking while filling out the health forms, a gyroscope or the like will detect the movement and generate sensor data based on the movement. The sensor data is then transmitted to the server health form application which recognizes that the shaking might be related to latent tremors the patient is experiencing. Based on the sensor data indicating tremors, the server health form application updates the customized health form to include questions related to tremors. At 508, the updated customized health form is transmitted to the client health form application executing on the client computing device for display. At 510, responsive to receiving data comprising responses to the updated customized health form from the client health form application, the server health form application transmits the responses to the server EHR, wherein the responses are stored as clinical data assigned to the patient identifier. The methodology 500 concludes at 512.

Figure 6:
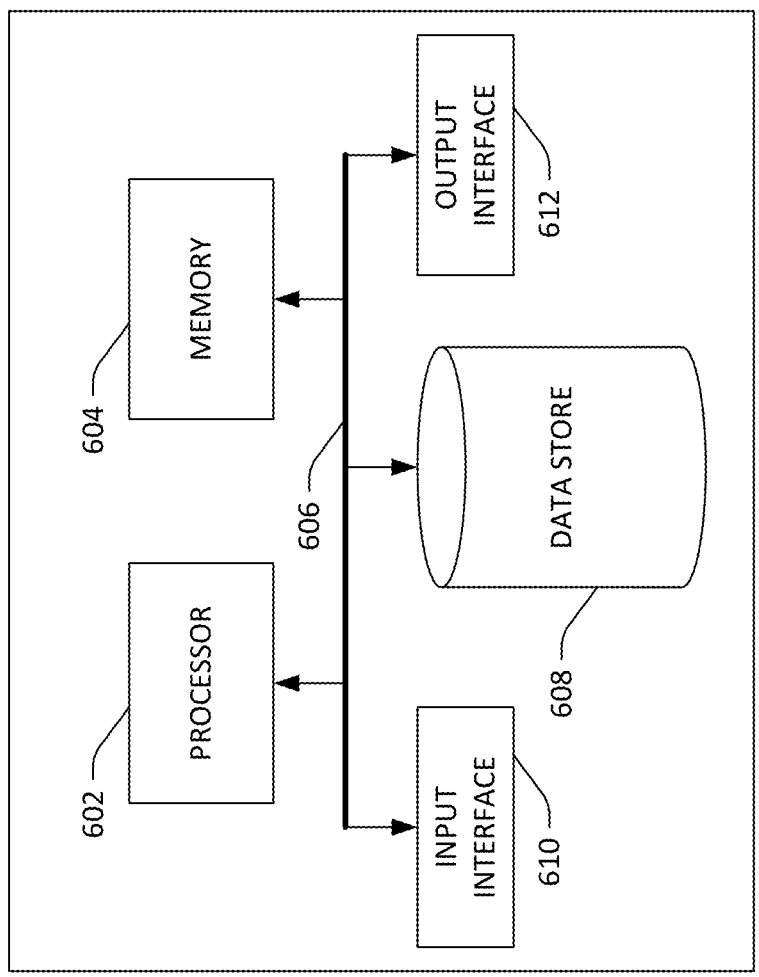
FIG. 6 is an exemplary computing system.

Referring now to FIG. 6, a high-level illustration of an exemplary computing device 600 that can be used in accordance with the systems and methodologies disclosed herein is illustrated. For instance, the computing device 600 may be used in a system that facilitates generating a customized health form for a based on clinical data assigned to the patient. By way of another example, the computing device 600 can be used in a system that updating a previously generated customized health form for a patient based on a sensor data received from a client computing device being operated by the patient. The computing device 600 includes at least one processor 602 that executes instructions that are stored in a memory 604. The instructions may be, for instance, instructions for implementing functionality described as being carried out by one or more components discussed above or instructions for implementing one or more of the methods described above. The processor 602 may access the memory 604 by way of a system bus 606. In addition to storing executable instructions, the memory 604 may also store clinical data, form data, sensor data, etc.

The computing device 600 additionally includes a data store 608 that is accessible by the processor 602 by way of the system bus 606. The data store 608 may include executable instructions, clinical data, form data, sensor data, etc. The computing device 600 also includes an input interface 610 that allows external devices to communicate with the computing device 600. For instance, the input interface 610 may be used to receive instructions from an external computer device, from a user, etc. The computing device 600 also includes an output interface 612 that interfaces the computing device 600 with one or more external devices. For example, the computing device 600 may display text, images, etc. by way of the output interface 612.

It is contemplated that the external devices that communicate with the computing device 600 via the input interface 610 and the output interface 612 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 600 in a manner free from constraints imposed by input devices such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 600 may be a distributed system. Thus, for instance, several devices may be in communication by way of a network connection and may collectively perform tasks described as being performed by the computing device 600.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A server computing device, comprising:
   a processor; and
   memory storing a server electronic health records (EHR) application and a server health form application that is in communication with the server EHR application, wherein the server health form application, when executed by the processor, is configured to cause the processor to perform acts comprising:
      receiving an indication that a patient has arrived for an appointment, wherein the indication comprises a patient identifier;
      responsive to receiving the indication, transmitting a request to the server EHR application, the request being for clinical data about the patient that is stored in a database maintained by the server EHR application;
      responsive to transmitting the request, receiving the clinical data about the patient from the server EHR application;
      responsive to receiving the clinical data about the patient, generating, based on the clinical data about the patient, a customized health form for the patient, the customized health form comprising questions pertaining to the patient, wherein the questions are based on the clinical data about the patient, and further wherein the customized health form is configured to receive answers to the questions from the patient;
      transmitting the customized health form to a client health form application executing on a client computing device that is in network communication with the server computing device, where the customized health form is transmitted for presentment to the patient on a display of the client computing device;
      receiving, from the client health form application, sensor data generated by a camera of the client computing device, wherein the sensor data is generated as the answers are received in the customized health form from the patient, wherein the sensor data pertains to eye health of the patient at the time that the answers are received from the patient, wherein the sensor data comprises an image captured by the camera, and further wherein the image indicates that the patient is squinting while viewing the customized health form;
      while the customized health form is displayed on the display, identifying an additional question for the patient to answer based upon the sensor data, wherein the additional question pertains to the eye health of the patient; and
      transmitting data to the client health form application that causes the customized health form to be updated to display the additional question to the patient.

2. The server computing device of claim 1, wherein the clinical data about the patient identifies a primary language of the patient, and further wherein the customized health form is generated in the primary language of the patient.

3. The server computing device of claim 1, wherein the client computing device further includes a gyroscope, wherein the the gyroscope outputs gyroscope data, wherein the gyroscope data indicates that the client computing device is being shaken while the patient is viewing the customized health form, the acts further comprising:
   while the customized health form is displayed on the display, identifying a second question for the patient to answer based upon the gyroscope data, wherein the second question pertains to whether the patient experiences tremors.

4. The server computing device of claim 3, wherein the data transmitted to the client health form application causes the client health form application to correct for movement of the client computing device caused by the tremors being experienced by the patient.

5. The server computing device of claim 1, wherein the questions are initially displayed in a first font size on the display, wherein the data transmitted to the client health form application causes the questions and the additional question to be displayed on the display in a second font size that is larger than the first font size.

6. The server computing device of claim 1, the acts further comprising:
   receiving, from the client health form application, the answers to the questions and an answer to the additional question in the customized health form; and
   storing the answers to the questions and the answer to the additional question in the customized health form as part of the clinical data about the patient stored in the database maintained by the server EHR application.

7. The server computing device of claim 6, the acts further comprising:
   responsive to receiving the answers to the questions and the answer to the additional question in the customized health form, generating a second customized health form comprising second questions pertaining to the patient that are based on the clinical data about the patient and the answers to the questions and the answer to the additional question in the customized health form, wherein the second customized health form is configured to receive second answers to the second questions as input from the patient; and transmitting the second customized health form to the client health form application for presentment to the patient on the display of the client computing device.

8. A method performed by a processor of a server computing device while the processor executes a server health form application, the method comprising:

receiving an indication that a patient has arrived for an appointment, wherein the indication comprises a patient identifier;

responsive to receiving the indication, transmitting a request to a server electronic health records (EHR) application for clinical data about the patient stored in a database maintained by the server EHR application;

responsive to transmitting the request, receiving the clinical data about the patient from the server EHR application;

responsive to receiving the clinical data about the patient, generating, based on the clinical data about the patient, a customized health form for the patient, the customized health form comprising questions pertaining to the patient that are based on the clinical data about the patient, wherein the customized health form is configured to receive answers to the questions as input from the patient;

transmitting the customized health form to a client health form application executing on a client computing device that is in network communication with the server computing device for presentment to the patient on a display of the client computing device;

receiving, from the client health form application, gyroscope data generated by a gyroscope of the client computing device as the customized health form receives the answers as the input from the patient, wherein the gyroscope data that indicates that the client computing device is being shaken while the patient is viewing the customized health form;

while the customized health form is displayed on the display, identifying an additional question for the patient to answer based upon the gyroscope data, wherein the additional question pertains to whether the patient experiences tremors; and transmitting data to the client health form application that causes the customized health form to be updated to display the additional question to the patient.

9. The method of claim 8, wherein the data transmitted to the client health form application causes the client health form application to correct for movement of the client computing device caused by the tremors being experienced by the patient.

10. The method of claim 8, wherein the client computing device comprises a camera, wherein the camera outputs an image captured by the camera, wherein the image indicates that the patient is squinting while viewing the customized health form, the method further comprising:

identifying a second question for the patient to answer based upon the image, wherein the second question pertains to eye health.

11. The method of claim 10, wherein the questions are initially displayed in a first font size on the display, wherein the data transmitted to the client health form application causes the questions and the additional question to be displayed on the display in a second font size that is larger than the first font size.

12. The method of claim 8, further comprising:

receiving, from the client health form application, the answers to the questions and an answer to the additional question in the customized health form; and storing the answers to the questions and the answer to the additional question in the customized health form as part of the clinical data about the patient stored in the database maintained by the server EHR application.

13. The method of claim 12, further comprising:

responsive to receiving the answer to the questions and the answer to the additional question in customized health form, generating a second customized health form comprising second questions pertaining to the patient that are based on the clinical data about the patient and the answers to the questions and the answer to the additional question in the customized health form, wherein the second customized health form is configured to receive second answers to the second questions as input from the patient; and transmitting the second customized health form to the client health form application for presentment to the patient on the display of the client computing device.

14. A computer-readable storage medium comprising a server health form application that, when executed by a processor of a server computing device, causes the processor to perform acts comprising:

receiving an indication that a patient has arrived for an appointment, wherein the indication comprises a patient identifier;

responsive to receiving the indication, transmitting a request to a server EHR application for clinical data about the patient stored in a database maintained by the server EHR application;

responsive to transmitting the request, receiving the clinical data about the patient from the server EHR application;

responsive to receiving the clinical data about the patient, generating, based on the clinical data about the patient, a customized health form for the patient, the customized health form comprising questions pertaining to the patient that are based on the clinical data about the patient, wherein the customized health form is configured to receive answers to the questions as input from the patient;

transmitting the customized health form to a client health form application executing on a client computing device that is in network communication with the server computing device for presentment to the patient on a display of the client computing device;

subsequent to transmitting the customized form to the client health form application, receiving, from the client health form application, an image generated by a camera of the client computing device as the customized health form receives the answers as the input from the patient;

while the customized health form is displayed on the display, identifying an additional question for the patient to answer based upon the image, wherein the additional question pertains to eye health of the patient;

transmitting data to the client health form application that causes the customized health form to be updated to display the additional question to the patient;

receiving, from the client health form application, the answers to the questions and an answer to the additional question in the customized health form; and storing the answers to the questions and the answer to the additional question in the customized health form as part of the clinical data about the patient stored in the database maintained by the server EHR application.

15. The computer-readable storage medium of claim 14, the acts further comprising:
generating a second customized health form comprising second questions pertaining to the patient that are based on the clinical data about the patient and the answers to the questions and the answer to the additional question in the customized health form, wherein the second customized health form is configured to receive second answers to the second questions as input from the patient; and
transmitting the second customized health form to the client health form application for presentment to the patient on the display of the client computing device.

16. The computer-readable storage medium of claim 14, the acts further comprising:
subsequent to transmitting the customized form to the client health form application, receiving, from the client health form application, gyroscope data output by a gyroscope of the client computing device, wherein the gyroscope data indicates that the client computing device is being shaken while the patient is viewing the customized health form;
while the customized health form is displayed on the display, identifying a second question for the patient to answer based upon the gyroscope data, wherein the second question pertains to whether the patient experiences tremors, where the data causes the customized health form to be updated to display the second question to the patient.

17. The computer-readable storage medium of claim 16, wherein the data transmitted to the client health form application causes the client health form application to correct for movement of the client computing device caused by the tremors being experienced by the patient.

* * * * *